(12) United States Patent
Asada et al.

(10) Patent No.: US 8,032,965 B2
(45) Date of Patent: Oct. 11, 2011

(54) ELECTRIC TOOTHBRUSH

(75) Inventors: Yuji Asada, Kyoto (JP); Tadashi Tone, Kyoto (JP); Jun Shimoyama, Uji (JP); Kuniyoshi Takahashi, Kusatsu (JP); Toshiyuki Iwahori, Mishima-gun (JP); Yumiko Nagase, Urayasu (JP)

(73) Assignee: Omron Healthcare Co., Ltd., Kyoto (JP)

( * ) Notice: Subject to any disclaimer, the term of this patent is extended or adjusted under 35 U.S.C. 154(b) by 609 days.

(21) Appl. No.: 12/179,952

(22) Filed: Jul. 25, 2008

(65) Prior Publication Data

US 2009/0025156 A1    Jan. 29, 2009

(30) Foreign Application Priority Data

Jul. 27, 2007    (JP) ................. 2007-195549

(51) Int. Cl.
*A46B 13/02* (2006.01)
(52) U.S. Cl. ...................... 15/22.1; 15/167.1
(58) Field of Classification Search ............ 15/22.1, 15/22.2, 22.4, 88.1–88.4, 167.1
See application file for complete search history.

(56) References Cited

U.S. PATENT DOCUMENTS

| | | | |
|---|---|---|---|
| 5,493,747 A | | 2/1996 | Inakagata et al. |
| 5,613,259 A | * | 3/1997 | Craft et al. ............ 15/22.1 |
| 2002/0100129 A1 | * | 8/2002 | Huen ............ 15/22.1 |
| 2003/0115693 A1 | | 6/2003 | Grez |
| 2005/0235438 A1 | | 10/2005 | Motohashi |
| 2006/0168745 A1 | * | 8/2006 | Kobayashi et al. ............ 15/22.1 |
| 2009/0070948 A1 | * | 3/2009 | Bax ............ 15/22.2 |
| 2010/0186179 A1 | * | 7/2010 | Miller et al. ............ 15/22.2 |

FOREIGN PATENT DOCUMENTS

| | | |
|---|---|---|
| DE | 10255722 | 6/2004 |
| DE | 102004022663 | 12/2005 |
| JP | 6510675 | 10/1992 |
| JP | 07116027 | 5/1995 |
| JP | 2003-093416 | 4/2003 |
| JP | 2007514397 | 5/2007 |
| WO | 9216160 | 10/1992 |
| WO | 2005058188 | 6/2005 |
| WO | 2006/016419 | 2/2006 |
| WO | 2007/072365 | 6/2007 |

OTHER PUBLICATIONS

RU patent application No. 2008130815/14(038269), Decision on Grant mailed Nov. 12, 2009.

* cited by examiner

*Primary Examiner* — Dung Van Nguyen
(74) *Attorney, Agent, or Firm* — Weaver Austin Villeneuve & Sampson LLP

(57) ABSTRACT

An electric toothbrush includes a driving source; a vibrating member having a brush; a transmission mechanism which converts an output of the driving source into vibration of the vibrating member; and a control unit that controls the output of the driving source. The vibrating member has a first resonance point in which the brush resonates in a first direction, and a second resonance point in which the brush resonates in a second direction; and the control unit has a first operation mode which controls the output of the driving source so that a resonance in the first direction is generated, and a second operation mode which controls the output of the driving source so that a resonance in the second direction is generated.

18 Claims, 8 Drawing Sheets

ELECTRIC TOOTHBRUSH

BACKGROUND OF THE INVENTION

1. Field of the Invention

The present invention relates to an electric toothbrush.

2. Description of the Related Art

There is known an electric toothbrush of a type for toothbrushing (removing plaque) by placing a high speed vibration brush against a tooth surface. In this type of the electric toothbrush, various driving mechanisms and driving methods have been proposed for an improvement in plaque removing power and an improvement in the sense of medical treatment.

Japanese Patent Application National Publication (Laid-Open) No. 6-510675 (WO92/16160) discloses a configuration which vibrates a lever arm provided with a brush to the right and the left at a frequency substantially equivalent to a resonance frequency in a magnetically driven electric toothbrush. Japanese Patent Application National Publication (Laid-Open) No. 2007-514397 (WO2005/058188) discloses a configuration which periodically changes amplitude of a brush head in a range of 5 to 30% by changing a driving frequency centered on a resonance frequency which is deviated by approximately 0 to 5 Hz from a resonance frequency of a toothbrush. Furthermore, Japanese Patent Application Laid-Open (JP-A) No. 7-116027 (U.S. Pat. No. 5,493,747) discloses a configuration which controls a frequency of a brush by changing the number of rotation of a motor on the basis of a detection result of toothbrushing pressure.

SUMMARY OF THE INVENTION

An object of the present invention is to provide a technique for further improving plaque removing power and the sense of medical treatment of an electric toothbrush.

Furthermore, a further object of the present invention is to provide a technique for further improving plaque removing power and the sense of medical treatment of an electric toothbrush without causing complexity in configuration, cost increase, and an increase in electric power consumption.

To attain the above mentioned object, the present invention adopts the following configuration.

According to the present invention, there is provided an electric toothbrush which includes: a driving source; a vibrating member having a brush; a motion transmission mechanism which converts an output of the driving source into vibration of the vibrating member; and a control unit that controls the output of the driving source. The vibrating member has a first resonance point in which the brush resonates in a first direction, and a second resonance point in which the brush resonates in a second direction; and the control unit has a first operation mode which controls the output of the driving source so that a resonance in the first direction is generated, and a second operation mode which controls the output of the driving source so that a resonance in the second direction is generated.

In the first operation mode, the control unit controls the output of the driving source so that a frequency of the vibrating member is the first resonance point or adjacent thereto. Similarly, in the second operation mode, the control unit controls the output of the driving source so that the frequency of the vibrating member is the second resonance point or adjacent thereto.

In the operation mode which uses resonance (hereinafter, referred to as "resonance operation mode") as the above mentioned first and second operation modes, amplitude of the brush becomes larger than that in the operation mode which does not use resonance (hereinafter, referred to as "normal operation mode"), and therefore, an improvement in the plaque removing power and the sense of medical treatment can be achieved. In addition, a plurality of resonance operation modes which are different in resonance direction can be used, and therefore, a higher plaque removing effect can be obtained if a brushing method (brushing direction) is switched in response to a medical treatment portion, for example.

Furthermore, in the present invention, a plurality of resonance operation modes are achieved by only output control of the driving source, and therefore, special mechanisms and parts are not required in a driving system and a transmission system. Consequently, it does not cause complexity in configuration and cost increase of the electric toothbrush. Further, a resonance phenomenon is used, and therefore, an improvement in amplitude (improvement in plaque removing power) can be achieved in electric power consumption equivalent to that in the normal operation mode and it becomes efficient.

In this case, the control unit may repeat the first operation mode and the second operation mode. A brushing direction is automatically switched, and therefore, a superior plaque removing effect can be achieved as compared with brushing in a single direction.

It is preferred that the first direction is a direction parallel to a brush face; and the second direction is a direction perpendicular to the brush face. In this case, a "brush face" means a virtual plane which is intersected with brush fiber and is located at a tip portion of the fiber. In the resonance in the first direction, bristle tips of the brush are wiggled in a direction parallel to a treatment portion, and therefore, there can be obtained a high effect in brushing of a periodontal pocket. In the resonance in the second direction, bristle tips of the brush are wiggled in a direction perpendicular to the treatment portion, and therefore, there can be obtained a high effect in brushing of an aperture between two neighboring teeth, a periodontal pocket, and a tooth surface.

It is preferred that the first resonance point is characteristics dependent on the motion transmission mechanism; and the second resonance point is characteristics dependent on the brush.

It is preferred that the control unit detects a load acting on the brush, and adjusts the output of the driving source in response to the detected load. The reason is that vibration characteristics of the vibrating member change dependent on the load acting on the brush.

It is preferred that the motion transmission mechanism is encased in the vibrating member, and the vibrating member is mounted to an electric toothbrush body through an elastic member. According to this configuration, since the motion transmission mechanism is encased in the vibrating member, brush neighborhood is efficiently vibrated. On the other hand, the vibration of the vibrating member becomes hard to be transmitted to the electric toothbrush body through the intervention of the elastic member, and therefore, it becomes possible to improve usability.

It is preferred that the driving source is a motor; the motion transmission mechanism is an eccentric shaft coupled to a rotation shaft of the motor; and the vibrating member has a stem having a bearing of the eccentric shaft. In the electric toothbrush of such a driving principle, the vibrating member (brush) two-dimensionally vibrates in a plane perpendicular to the rotation shaft. Then, resonances are appeared in two directions substantially intersecting in the vibration plane, respectively. The two directions can be used as the above-described first and the second directions.

In addition, the present invention can be configured by mutually combining the above respective means and procedures as much as possible.

The present invention can further improve plaque removing power and the sense of medical treatment of the electric toothbrush. Furthermore, the present invention does not cause complexity in configuration, cost increase, and an increase in electric power consumption.

DESCRIPTION OF THE EMBODIMENTS

Preferred embodiments of the present invention will be exemplarily described in detail with reference to the accompanying drawings.

First Embodiment

<Configuration of Electric Toothbrush>

Figure 1:
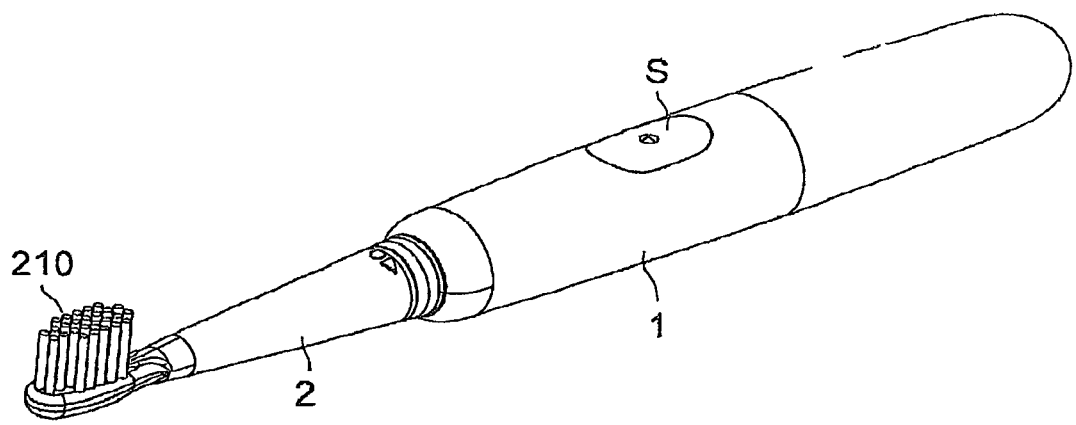
FIG. 1 is a perspective view showing an appearance of an electric toothbrush.
Figure 2:
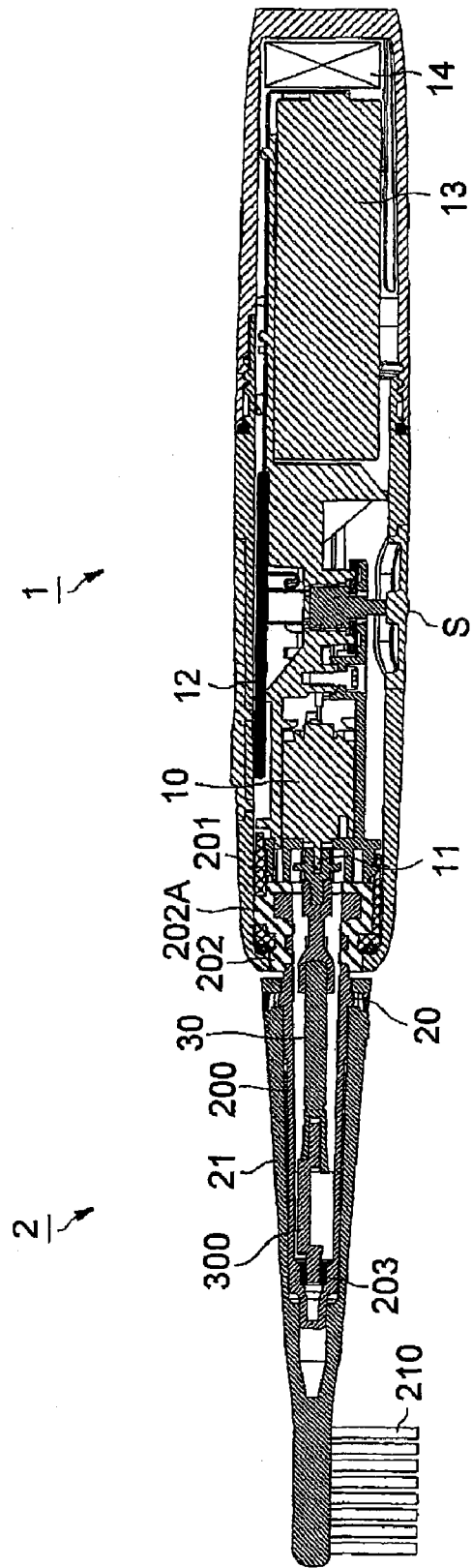
FIG. 2 is a cross sectional view showing an internal configuration of the electric toothbrush.
Figure 3:
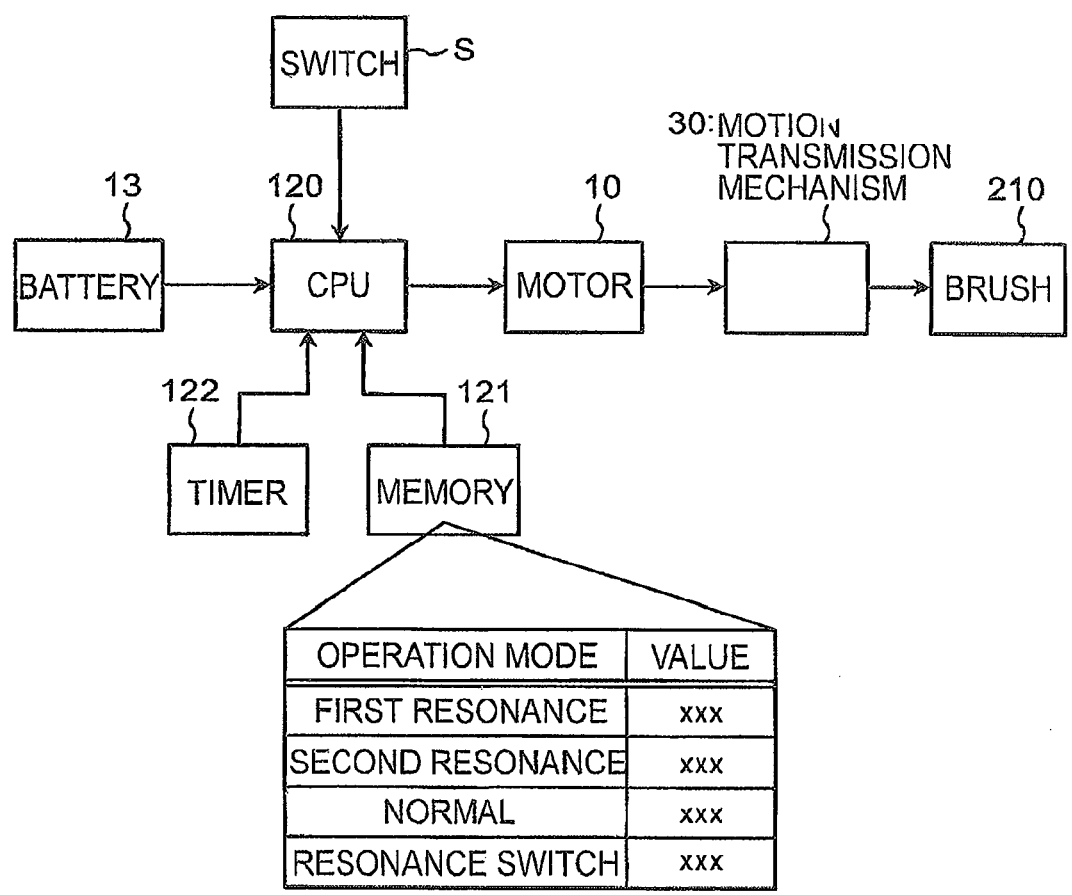
FIG. 3 is a block diagram of a first embodiment.

Referring to FIGS. 1 to 3, a configuration of an electric toothbrush will be described. FIG. 1 is a perspective view showing an appearance of the electric toothbrush; FIG. 2 is a cross sectional view showing an internal configuration of the electric toothbrush; and FIG. 3 is a block diagram.

The electric toothbrush includes an electric toothbrush body 1 (hereinafter, referred to as merely "body 1") which incorporates a motor 10 serving as a driving source, and a vibrating member 2 having a brush 210. The body 1 is substantially cylindrical, and doubles as a handle portion which is gripped by a user's hand during toothbrushing.

The body 1 is provided with a switch S which is for performing ON/OFF control of a power supply and switching of operation modes. Furthermore, a motor 10 serving as a driving source, a driving circuit 12 which is for controlling the number of rotation of the motor 10, a rechargeable battery 13 serving as a 2.4 V power supply, a charging coil 14, and the like are provided in the inside of the body 1. In the case where the rechargeable battery 13 is charged, it is possible to charge in non-contact manner because of electromagnetic induction by merely mounting the body 1 to a charger (not shown in the drawing). The driving circuit 12 has a central processing unit (CPU) 120, a memory 121 which stores programs and various setting values, a timer 122, and the like, as shown in FIG. 3.

The vibrating member 2 includes a stem portion 20 fixed to the body 1 side, and a brush part 21 attached to the stem portion 20. A brush 210 is implanted at the head of the brush part 21. Since the brush part 21 is a consumable part, the brush part 21 is configured to be detachable/attachable from/to the stem portion 20 so as to be exchangeable with a new one.

The stem portion 20 is composed of a stem 200 and a holder 201, both of which are made of resin material; and an elastic member 202 made of elastomer. The elastic member 202 is preferable to be integrally formed to the stem 200 and the holder 201 by insert molding. The elastic member 202 intervenes between the stem 200 and the holder 201, and is provided with a plurality of (for example, three) protrusion portions 202A which are respectively protruded from a plurality of through-holes provided in the holder 201. The stem portion 20 is positioned by three point contacts by three protrusion portions 202A of the elastic member 202 with respect to an outer case of the body 1. In this manner, the vibrating member 2 of the present embodiment is mounted to the body 1 through the elastic member 202.

The stem 200 is a cylindrical member whose tip (brush side end) is closed, and has a bearing 203 at the tip in the inside of the cylinder. The tip of an eccentric shaft 30 coupled to a rotation shaft 11 of the motor 10 is inserted to the bearing 203 of the stem 200. The eccentric shaft 30 has a weight 300 in the vicinity of the bearing 203, and the center of gravity of the eccentric shaft 30 is out of alignment from its rotation center. In addition, a minute clearance is set between the tip of the eccentric shaft 30 and the bearing 203.

<Fundamental Operation of Electric Toothbrush>

The fundamental operation of the electric toothbrush will be described.

When the power supply is in an ON state, the CPU 120 supplies a pulse width modulation signal (PWM signal) to the motor 10, and the rotation shaft 11 of the motor 10 is rotated. With a rotation of the rotation shaft 11, the eccentric shaft 30 is also rotated, however, the eccentric shaft 30 performs a motion as though swirling around the rotation center due to the shifted center of gravity. Consequently, the tip of the eccentric shaft 30 repeatedly hits against an internal wall of the bearing 203, and the stem 200 and the brush part 21 attached thereto are vibrated in a high speed. That is, the eccentric shaft 30 has a role of a motion transmission mechanism (motion conversion mechanism) which converts an output (rotation) of the motor 10 into vibration of the vibrating member 2. Plaque can be removed by holding the body 1 by hand and by placing a high speed vibration brush 210 against teeth. In addition, the CPU 120 monitors a continuous operation time using the timer 122, and the vibration of the brush is automatically stopped after a lapse of a predetermined time (for example, for two minutes).

In the electric toothbrush of the present embodiment, the eccentric shaft 30 serving as the motion transmission mechanism is encased in the vibrating member 2 and, more particularly, the weight 300 is arranged in the vicinity of the brush 210. Consequently, a portion of the brush 210 can be efficiently vibrated. On the other hand, the vibrating member 2 (stem portion 20) is mounted to the body 1 through the elastic member 202, and therefore, the vibration of the vibrating member 2 becomes hard to be transmitted to the body 1. Consequently, vibration of the body 1 and hand during toothbrushing can be reduced and it becomes possible to improve usability.

<Description of Vibration Characteristics>

Figure 4:
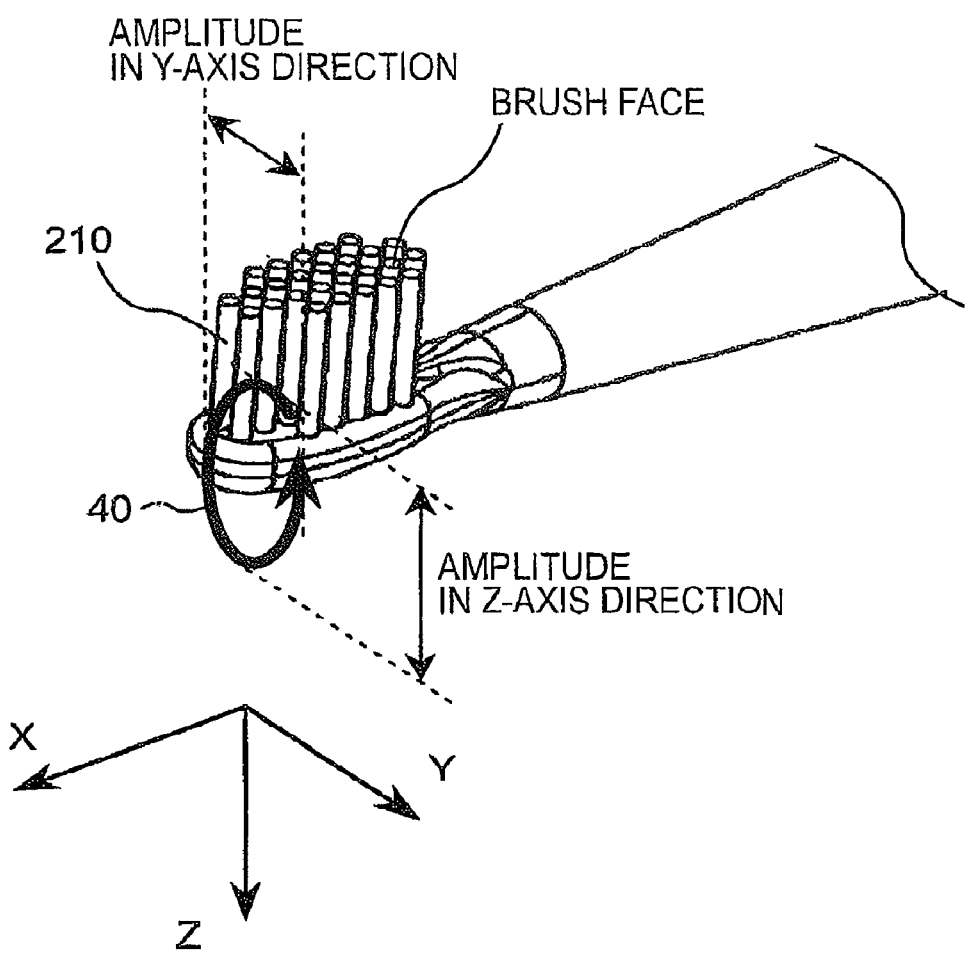
FIG. 4 is a view typically showing vibration of the brush.

In the electric toothbrush of the present embodiment, as described above, vibration of the brush 210 is generated by using swirling motion of the eccentric shaft 30. In the case of such a driving principle, the brush 210 can be two-dimensionally vibrated in a plane perpendicular to the rotation shaft of the motor. FIG. 4 typically shows vibration orbits of the brush (X-axis: the motor rotation shaft, Y-axis: a direction perpendicular to the rotation shaft and parallel to the brush face, and Z-axis: a direction perpendicular to the brush face). In an example shown in the drawing, the brush 210 is vibrated in YZ plane in an elliptical orbit 40. The "brush face" means a virtual plane which is intersected with brush fiber and is located at a tip portion of the fiber.

Figure 5:
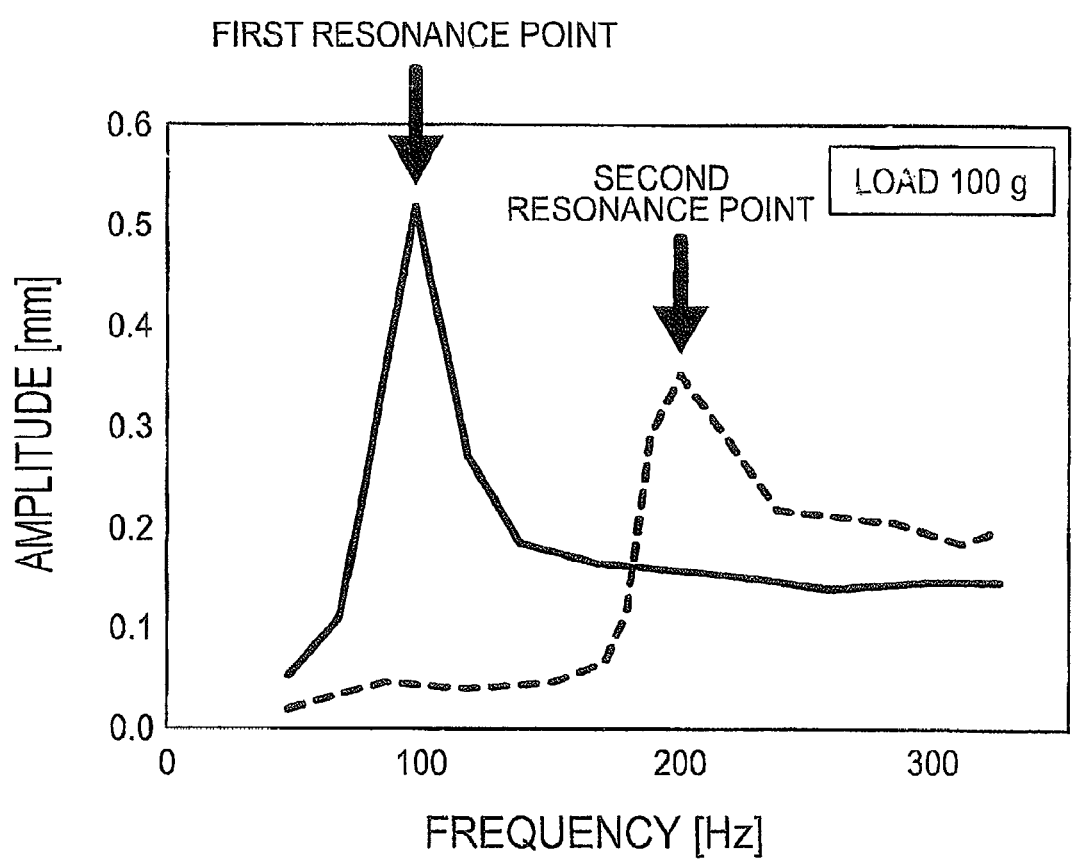
FIG. 5 is a graph showing resonance points in case of a load of 100 g.

The present inventors have found that the electric toothbrush has vibration characteristics as shown in FIG. 5, by observing and analyzing the vibration of the brush while frequency (the number of motor rotation) is changed. In addition, FIG. 5 shows a relationship between the frequency and amplitude in a state where a load of 100 g is applied to the brush in the Z-axis direction. A lateral axis is frequency [Hz], a longitudinal axis is amplitude [mm], a graph in a solid line represents the amplitude in the Y-axis direction (lateral direction), and a graph in a dashed line represents the amplitude in the Z-axis direction (longitudinal direction).

As can be seen from the graphs shown in FIG. 5, the electric toothbrush of the present embodiment has at least two resonance points (resonance frequencies), and resonance directions at the respective resonance points are different. More specifically, a resonance in the Y-axis direction that is a resonance direction parallel to the brush face is generated at a resonance point (first resonance point: approximately 100 Hz) whose frequency is low-side; and a resonance in the Z-axis direction that is a resonance direction perpendicular to the brush face is generated at a resonance point (second resonance point: approximately 200 Hz) whose frequency is high-side.

The reason why a plurality of resonances which are different in direction are appeared is considered that it is largely dependent on a structure of the electric toothbrush and its driving principle. The present inventors have obtained a finding that the first resonance point is characteristics mainly dependent on the motion transmission mechanism and the second resonance point is characteristics mainly dependent on the brush, by repeating experiments while the configuration of the eccentric shaft and the brush is changed. In other words, it is found that the frequency and amplitude at the first resonance point can be adjusted by changing the structure or shape (in short, position, size, mass, or the like of the weight of the eccentric shaft) of the motion transmission mechanism; and the frequency and amplitude at the second resonance point can be adjusted by changing the structure or shape of the brush.

<Description of Operation Mode>

The electric toothbrush of the present embodiment has a plurality of operation modes whose driving frequencies are different. The operation modes are switched in order from an OFF state of the power supply every pushing operation of the switch S, and are looped back to the OFF state. As shown in FIG. 3, setting values corresponding to the respective operation modes are preliminarily stored in the memory 121. The setting values are parameters corresponding to driving frequencies of the respective operation modes, and their specific values are determined on the basis of results of experiments as shown in FIG. 5.

When the operation mode is switched, the CPU 120 reads a corresponding setting value from the memory 121, and a duty ratio of the PWM signal is determined in accordance with the value. When the duty ratio is increased, the number of rotation of the motor 10 is increased, and as a result, a frequency of the brush 210 is increased. In this manner, in the present embodiment, the driving circuit 12 has a role of a control unit for controlling the output (the number of rotation) of the motor 10 and the frequency of the brush 210.

Figure 6A:
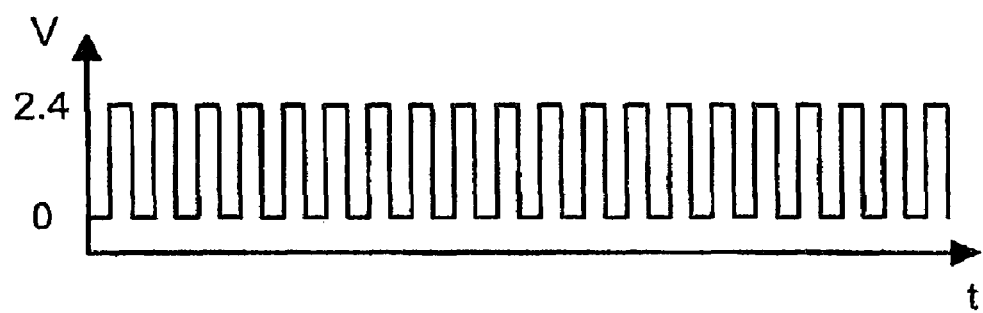
FIGS. 6A to 6C are views showing waveforms of PWM signals in the respective operation modes.
Figure 6B:
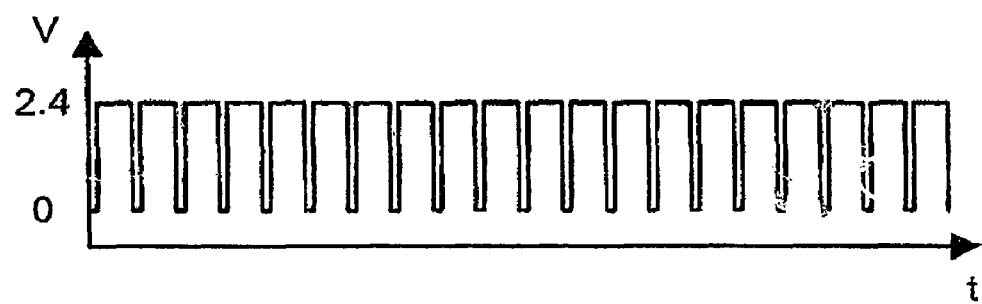
Figure 6C:
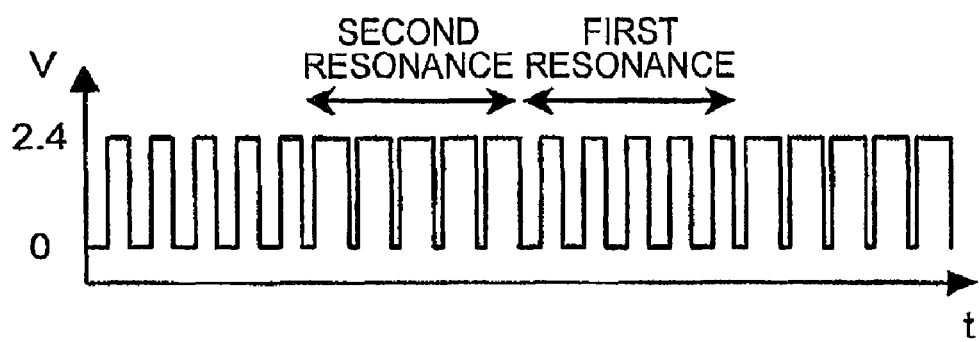

Now, features of the respective operation modes will be described with reference to FIG. 5 and FIGS. 6A to 6C. FIGS. 6A to 6C show one example of a waveform of the PWM signal in each of the operation modes.

(1) First Resonance Operation Mode

A first resonance operation mode is an operation mode which uses the first resonance point. The driving frequency is set to the first resonance point (approximately 100 Hz) or adjacent thereto. FIG. 6A shows a PWM signal (duty ratio: approximately 50%) of the first resonance operation mode. In the first resonance operation mode, amplitude in the Y-axis direction (lateral direction) of the brush 210 becomes higher than that of a normal operation mode, and accordingly, plaque removing power and the sense of medical treatment can be enhanced. More particularly, in the first resonance operation mode, bristle tips of the brush 210 are wiggled in a direction parallel to a treatment portion, and therefore, it is considered that there can be obtained a high effect in brushing of a periodontal pocket.

(2) Second Resonance Operation Mode

A second resonance operation mode is an operation mode which uses the second resonance point. The driving frequency is set to the second resonance point (approximately 200 Hz) or adjacent thereto. FIG. 6B shows a PWM signal (duty ratio: approximately 80%) of the second resonance operation mode. In the second resonance operation mode, amplitude in the Z-axis direction (longitudinal direction) of the brush 210 becomes higher than that of the normal operation mode, and accordingly, the plaque removing power and the sense of medical treatment can be enhanced. More particularly, in the second resonance operation mode, the bristle tips of the brush 210 are wiggled in a direction perpendicular to the treatment portion, and therefore, it is considered that there can be obtained a high effect in brushing of an aperture between two neighboring teeth, a periodontal pocket, and a tooth surface.

(3) Normal Operation Mode

The normal operation mode is an operation mode which does not use resonance. The driving frequency is set to between the first resonance point and the second resonance point (for example, 150 Hz). In addition, it may be switched by the switch S by providing multistep normal operation modes such as 120 Hz, 140 Hz, 160 Hz, and 180 Hz. Furthermore, it is preferable to provide normal operation modes of a frequency lower than the first resonance point and a frequency higher than the second resonance point.

(4) Resonance Switching Operation Mode

A resonance switching operation mode is an operation mode which alternately repeats the first resonance operation mode and the second resonance operation mode. More specifically, as shown in FIG. 6C, two operation modes are switched at a constant time interval (for example, approximately 0.2 sec interval). In this manner the bristle tips of the brush are placed against the treatment portion at various angles by automatically switching brushing directions, and therefore, a more superior plaque removing effect can be achieved as compared with brushing in a single direction.

As described above, according to the present embodiment, the plaque removing power and the sense of medical treatment can be improved. In addition, since a plurality of resonance operation modes which are different in resonance direction can be used, for example, if a brushing method (brushing direction) is switched in response to the medical treatment portion, a higher plaque removing effect can be obtained. Furthermore, a plurality of resonance operation modes are achieved by controlling only the number of rotation of the motor, and therefore, a special mechanism and parts are not required in a driving system and transmission system. Consequently, it does not cause complexity in configuration and cost increase of the electric toothbrush. Further, since a resonance phenomenon is used, the amplitude can be increased (improvement in plaque removing power) in electric power consumption equivalent to that of the normal operation mode, and it becomes efficient.

Second Embodiment

Figure 7:
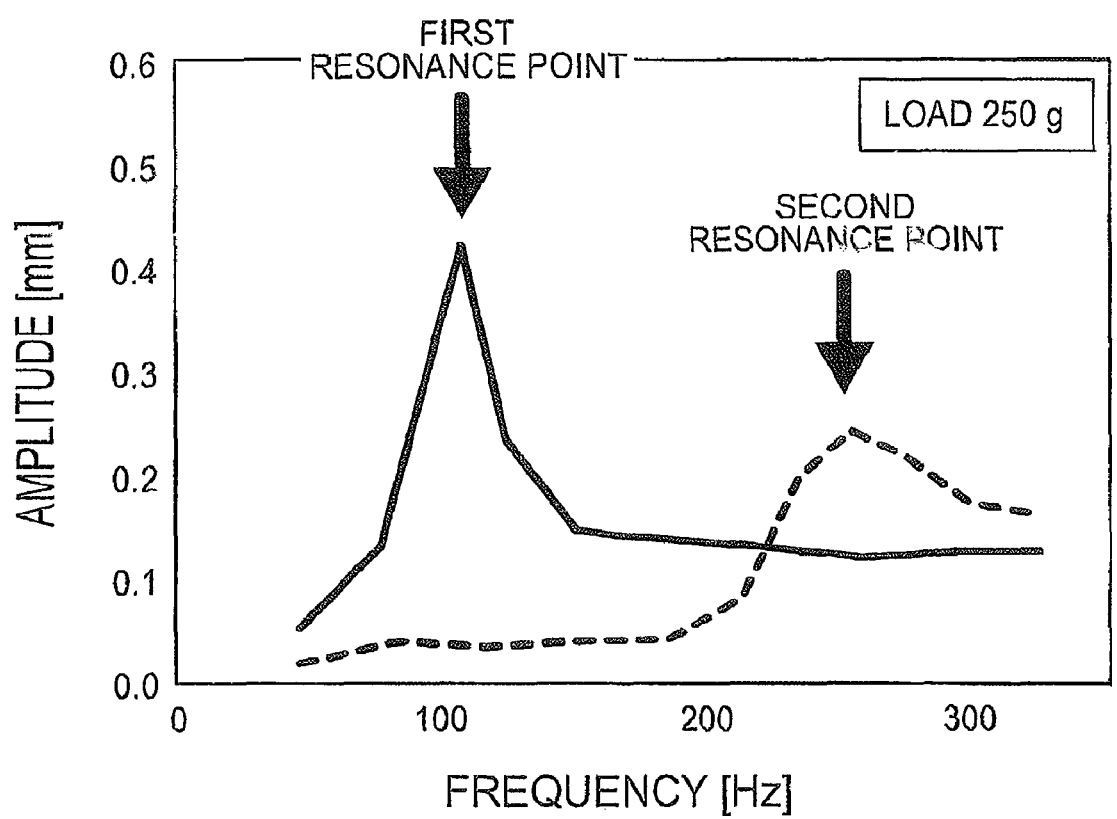
FIG. 7 is a graph showing resonance points in case of a load of 250 g.

In the above mentioned first embodiment, a single setting value is used in the respective operation modes. However, as shown in FIG. 7, when a load acting on the brush is changed, vibration characteristics of the brush are changed, and a resonance point position is changed. FIG. 7 shows vibration characteristics in the case of a load of 250 g, and a first resonance point appears at around 110 Hz and a second resonance point appears at around 250 Hz. As compared with the case of the load of 100 g (FIG. 5), it can be seen that both resonance points are increased. Consequently, in the second embodiment, the load acting on the brush is detected, and the number of rotation of a motor is adjusted in response to the magnitude of the load.

Figure 8:
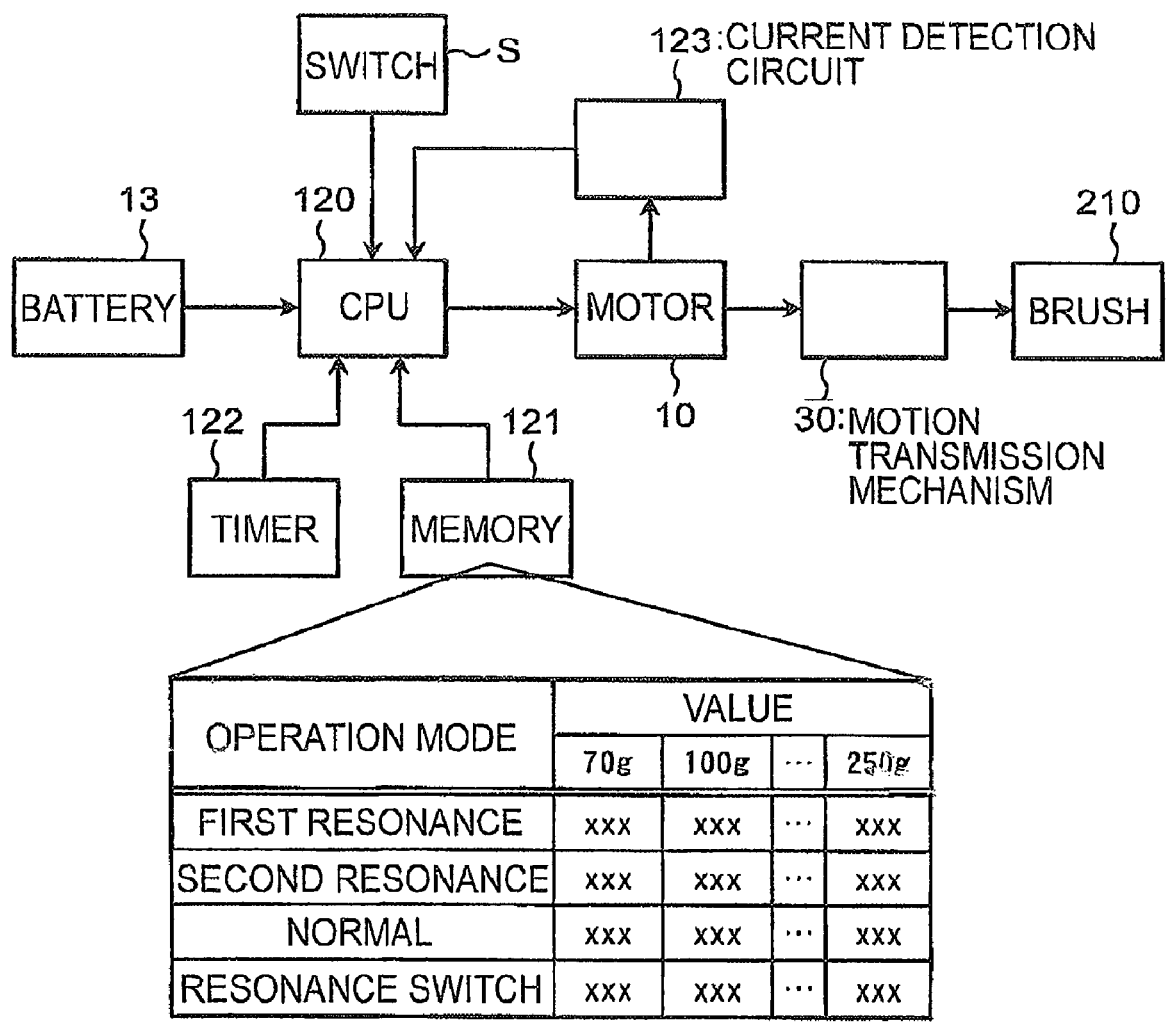
FIG. 8 is a block diagram of a second embodiment.

FIG. 8 is a block diagram of an electric toothbrush of the second embodiment. Different points from the first embodiment are that a current detection circuit 123 is provided and a plurality of setting values are stored in a memory 121 in response to the magnitude of the load.

The current detection circuit 123 is a circuit which detects a current value of a motor 10. The more strongly the brush is placed against a tooth surface, the larger the load acting on the brush will be. Then, when the load acting on the brush is increased, a load of the motor 10 is also increased, and accordingly, the current value flowing to the motor 10 is increased. Consequently, a CPU 120 can estimate the magnitude of the load acting on the brush 210 on the basis of a detection result of the current detection circuit 123.

The setting values corresponding to a range of the load from 70 g to 250 g are stored in the memory 121 according to the operation modes. In the present embodiment, setting values corresponding to preliminarily determined load values (typical values) such as loads of 70 g, 100 g, . . . , and 250 g are prepared. The CPU 120 selects an optimum one from the setting values on the basis of the load acting on the brush, or calculates an appropriate value by interpolating the setting values. In addition, in the case where the setting value can be expressed by a function of the magnitude of the load, it is also preferable to store parameters which represent the function in the memory.

By such a configuration, the number of rotation of the motor is appropriately adjusted in response to the magnitude of the load acting on the brush, and accordingly, a deviation of the resonance point dependent on the load can be covered and a resonance phenomenon can be correctly reproduced.

Modified Embodiment

The configurations of the above mentioned embodiments are nothing but exemplifications of one specific examples of the present invention. The scope of the present invention is not limited to the above-mentioned embodiments and is applicable to various changes and modifications within the scope of technical idea thereof.

For example, in the above mentioned embodiment, only two resonance points of the first resonance point and the second resonance point are used, however, three or more resonance points may be used. That is, if the vibrating member has a plurality of resonance points and a control unit has a plurality of resonance operation modes, those of which are included in the technical idea of the present invention.

Furthermore, in the resonance switching operation modes of the above mentioned embodiments, the first resonance operation mode and the second resonance operation mode are alternately switched, however, the switching mode is not limited to this. For example, a switching mode in which the normal operation mode intervenes between the two resonance operation modes and a switching mode which switches the plurality of the operation modes in a random manner are preferable. In addition, a switching interval may be appropriately changed. Further, it is preferable to provide a plurality of kinds of resonance switching operation modes whose switching manner and switching interval are different. Then, an operation mode which uses only one resonance point such as the first resonance operation mode and the second resonance operation mode is eliminated, and there may be provided only an operation mode which uses a plurality of resonance points such as resonance switching modes.

What is claimed is:

1. An electric toothbrush, comprising:
a motor;
a vibrating member having a brush;
a motion transmission mechanism which converts rotations of the motor into vibration of the vibrating member; and
a control unit that controls the number of rotations of the motor,
wherein the vibrating member has a first resonance point in which the brush resonates in a first direction, and a second resonance point in which the brush resonates in a second direction; and
wherein in a first operation mode, the control unit controls the number of rotations of the motor so that a resonance in the first direction is generated, and in a second operation mode, the control unit controls the number of rotations of the motor so that a resonance in the second direction is generated.

2. An electric toothbrush according to claim 1, wherein the control unit repeats the first operation mode and the second operation mode.

3. An electric toothbrush according to claim 2, wherein the first direction is a direction parallel to a brush face; and
the second direction is a direction perpendicular to the brush face.

4. An electric toothbrush according to claim 3, wherein the first resonance point is characteristics dependent on the motion transmission mechanism; and
the second resonance point is characteristics dependent on the brush.

5. An electric toothbrush according to claim 4, wherein the control unit detects a load acting on the brush, and adjusts rotations of the motor in response to the detected load.

6. An electric toothbrush according to claim 3, wherein the control unit detects a load acting on the brush, and adjusts rotations of the motor in response to the detected load.

7. An electric toothbrush according to claim 2, wherein the first resonance point is characteristics dependent on the motion transmission mechanism; and
the second resonance point is characteristics dependent on the brush.

8. An electric toothbrush according to claim 7, wherein the control unit detects a load acting on the brush, and adjusts rotations of the motor in response to the detected load.

9. An electric toothbrush according to claim 2,
wherein the control unit detects a load acting on the brush, and adjusts rotations of the motor in response to the detected load.

10. An electric toothbrush according to claim 1,
wherein the first direction is a direction parallel to a brush face; and
the second direction is a direction perpendicular to the brush face.

11. An electric toothbrush according to claim 10,
wherein the first resonance point is characteristics dependent on the motion transmission mechanism; and
the second resonance point is characteristics dependent on the brush.

12. An electric toothbrush according to claim 11,
wherein the control unit detects a load acting on the brush, and adjusts rotations of the motor in response to the detected load.

13. An electric toothbrush according to claim 10,
wherein the control unit detects a load acting on the brush, and adjusts rotations of the motor in response to the detected load.

14. An electric toothbrush according to claim 1,
wherein the first resonance point is characteristics dependent on the motion transmission mechanism; and
the second resonance point is characteristics dependent on the brush.

15. An electric toothbrush according to claim 14,
wherein the control unit detects a load acting on the brush, and adjusts rotations of the motor in response to the detected load.

16. An electric toothbrush according to claim 1,
wherein the control unit detects a load acting on the brush, and adjusts rotations of the motor in response to the detected load.

17. An electric toothbrush according to claim 1,
wherein the motion transmission mechanism is encased in the vibrating member; and
the vibrating member is mounted to an electric toothbrush body through an elastic member.

18. An electric toothbrush according to claim 1,
wherein the motion transmission mechanism is an eccentric shaft coupled to a rotation shaft of the motor; and
the vibration member has a stem having a bearing of the eccentric shaft.

\* \* \* \* \*